United States Patent [19]

Richardson

[11] Patent Number: 4,894,341
[45] Date of Patent: Jan. 16, 1990

[54] PRODUCTION OF CYANIDE HYDRATASE

[75] Inventor: Kenneth R. Richardson, Middlesbrough, England

[73] Assignee: Imperial Chemical Industries PLC, London, England

[21] Appl. No.: 10,489

[22] Filed: Feb. 3, 1987

[30] Foreign Application Priority Data

Feb. 19, 1986 [GB] United Kingdom ............... 8604069
Mar. 26, 1986 [GB] United Kingdom ............... 8607595

[51] Int. Cl.$^4$ .................. C12N 9/78; C12N 9/88; C12P 13/02; C12R 1/77
[52] U.S. Cl. .................................. 435/227; 435/232; 435/129; 435/929
[58] Field of Search ............... 435/232, 227, 929, 129

[56] References Cited

U.S. PATENT DOCUMENTS 4,402,831  9/1983  Beardsmore et al. ............... 210/606

FOREIGN PATENT DOCUMENTS 116423  1/1984  European Pat. Off. .

OTHER PUBLICATIONS

Japanese J. Ferment. Technol., vol. 45, No. 7, pp. 630–636 (1967).
Japanese J. Ferment. Technol., vol. 46, No. 10, pp. 807–813 (1968).
Japanese J. Ferment. Technol., vol. 47, No. 10, pp. 639–643 (1969).
Japanese J. Ferment. Technol., vol. 47, No. 10, pp. 644–650 (1969).
Japanese J. Ferment. Technol., vol. 48, No. 5, pp. 277–282 (1970).
Japanese J. Ferment. Technol., vol. 48, No. 5, pp. 283–290 (1970).
Archives of Biochem. & Biophys., 151, pp. 468–474 (1972).
Phytopathology, 67, pp. 1001–1006 (1977).

Primary Examiner—Elizabeth C. Weimar
Assistant Examiner—Charles L. Patterson, Jr.
Attorney, Agent, or Firm—Cushman, Darby & Cushman

[57] ABSTRACT

A process for the production of the enzyme cyanide hydratase which comprises aerobically cultivating cells of the fungal strain *Fusarium lateritium* Nees CMI 300533 and variants and mutants derives therefrom in an aqueous culture containing appropriate nutrients. A method of treating a cyanide-containing material to degrade the cyanide therein using cyanide hydratase produced by the process of the invention and a process for the production of a nitrilase enzyme are also claimed. *Fusarium lateritium* Nees CMI 300533 is deposited at The Commonwealth Mycological Institute, Kew, Richmond, Surrey, England under the terms of the Budapest Treaty.

11 Claims, No Drawings

PRODUCTION OF CYANIDE HYDRATASE

This invention relates to a process for the production of cyanide hydratase.

Certain fungi contain the enzyme cyanide hydratase EC No. 4.2.1.66 (otherwise known as formamide hydrolyase) which is capable of degrading cyanide to formamide (see for example Archives of Biochemistry and Biophysics, 151, pages 468 to 474, (1972) and Phytopathology, 67, pages 1001 to 1006, (1977)). It has been proposed to use such fungi in the microbiological treatment of cyanide containing effluents (see for example our European Patent No. 61249). A difficulty which up to the present has restricted the development of this proposed treatment is that many cyanide hydratase-containing fungi are pathogenic to plants including wheat and in particular to cyanogenic plants such as sorghum.

According to the present invention we provide a process for the production of the enzyme cyanide hydratase which comprises aerobically cultivating cells of the fungal strain *Fusarium lateritium* Nees CMI 300533 or of a variant or mutant strain derived therefrom in an aqueous culture containing sources of carbon and of appropriate inorganic nutrients and recovering fungal cells containing cyanide hydratase from the culture.

A method for the treatment of a cyanide-containing material to degrade the cyanide therein in which the material is treated with cyanide hydratase or a composition comprising cyanide hydratase characterised in that the cyanide hydratase has been produced by the process of the invention is also included in the scope of the invention.

The process of the invention can be a batch or, preferably, a continuous process. Suitably the process of the invention is a continuous process with the fungal cells being continuously cultivated at a temperature within the range 20° to 34° C., a pH within the range 4.5 to 7.5 and a dilution rate not greater than 0.25 $hr^{-1}$ and being continuously supplied with hydrogen cyanide and/or a source of cyanide ions and/or compounds which generate cyanide ions and/or hydrogen cyanide under fermentation conditions. Under the conditions of the process the cyanide ions will usually be present in the culture as hydrogen cyanide.

*Fusarium lateritium* Nees strain CMI 300533 has been deposited, 3 Feb. 1986, at the Commonwealth Mycological Institute, Ferry Lane, Kew, Richmond, Surrey. TW9 3AF, England. This strain is non-pathogenic to wheat and has the following morphological characteristics:

| Media | (1) | Potato Sucrose Agar (PSA) 250 grams of potatoes washed and diced, placed in pressure cooker at 15 lbs./square inch for 15 minutes. The decoction is then squeezed through two layers of muslin, 2% of Glucose and 2% of Agar are added to the turbid filtrate and the medium autoclaved and dispersed. |
|---|---|---|
| | (2) | Czapek-Dox (Modified) Agar (Oxoid) (CDA) "Oxoid" is a Registered Trade Mark |

Growth conditions: 25° C., several weeks
Rate of growth: 4.0 cm. in 3 days 3.0 cm in 3 days respectively
Character of growth:
Floccose, spreading colonies with white aerial mycelium.
Substratum on PSA greyish rose with patches of crimson to yellow. Tendency to be somewhat paler on CDA.

-continued

Occasionally deep red pigment produced, particularly on ageing. After one to two weeks the aerial mycelium tends to become brown and collapse. The colony then becomes rather slimy as sporodochia are formed the colour being pink to brown on PSA and salmon pink on CDA.
No exudate is formed and pigment formation tends to follow the mycelium colour.
Conidia: Microconidia not produced by this organism.
Macroconidia produced from single lateral phialides or multibranched conidiophores with short phialides.
In older cultures the conidiophores aggregate to form sporodochia, particularly on CDA. The conidia vary from falcate to curved fusoid dorsi-ventral, septation varying from 3 to 5, commonly 5 in younger cultures. Spore size varies from $25 - 50\ \mu \times 2.5\ \mu - 4.0\ \mu$.
The foot cell is often pedicellate, particularly in the longer 5 septate spores.
Swollen cells occur in the mycelium and occasionally chlamydospores occur intercalary, singly or in chains.

*Fusarium lateritium* Nees CMI 300533 exhibits in addition to cyanide hydratase activity an inducible nitrilase activity, i.e. it can be induced to catalyse the reactions whereby nitriles catalyse the reactions whereby nitriles (organic cyanides) are converted into the corresponding acids. It can therefore be used as a source of this enzyme. The production of a nitrilase enzyme by aerobically cultivating cells of *Fusarium lateritium* Nees CMI 300533 or a variant or mutant strain derived therefrom in an aqueous culture medium containing sources of carbon and appropriate inorganic nutrients is also included in the scope of the invention.

Fungi can be made to grow in two distinct forms, namely a ball or pellet form or in a dispersed form where the fungal cells are diffuse filamentous strands dispersed in the growth medium. For use in effluent treatment it is important that the fungus is grown in the dispersed, as opposed to ball or pellet, form. As growth in the pellet form is hampered by diffusion by nutrients and gases through the pellet, this makes cultivation inefficient. Preferably the conditions in which the cultivation part of the process of the invention is carried out are such as to encourage growth in the dispersed form.

In the cultivation part of the process the fungal cells may suitably be grown under conditions of carbon or oxygen limitation. Preferably however the conditions are such that growth takes place effectively under dual carbon and oxygen limitation. Preferably the culture medium is a defined medium, i.e. one containing only mineral salts in addition to the carbon source without any undefined organic materials such as yeast extract.

Any suitable carbon source may be used in the process but glucose is preferred. Preferred sources of nitrogen include ammonium sulphate and ammonium hydroxide and preferred sources of phosphorus include potassium phosphate and phosphoric acid. Preferably when the process is a continuous process, the main constituents of the culture medium are present in the medium supplied to the process during its steady state in concentrations within the following range:

| | |
|---|---|
| $H_3PO_4$ | 10–20 mM |
| $K_2SO_4$ | 800–1400 ppm |
| $MgSO_4 \cdot 7H_2O$ | 700–1200 ppm |
| Glucose $1.H_2O$ | 10.000–40.000 ppm |
| $(NH_4)_2 SO_4$ | 500–3000 ppm |

-continued

| Trace nutrients | 0.1 ppm–20 ppm |

A very suitable culture medium to be supplied to a continuous culture during steady state conditions has the following constitution:

| 1.1 M $H_3PO_4$ | 320 | ml/20 | L |
|---|---|---|---|
| Trace metals/Biotin | 10 | ml/20 | L |
| $K_2SO_4$ | 20 | g/20 | L |
| $MgSO_4 \cdot 7H_2O$ | 18 | g/20 | L |
| Glucose/$H_2O$ | 223 | g/20 | L |
| $(NH_4)_2SO_4$ | 50 | g/20 | L |

With the trace metals/Biotin solution having the following constitution (weights being per liter):

| $FeCl_3 \cdot 6H_2O$ | 9.6 g |
|---|---|
| $CuSO_4 \cdot 5H_2O$ | 3.6 g |
| $MnSO_4/4H_2O$ | 30.0 g |
| $ZnSO_4 \cdot 7H_2O$ | 38.0 g |
| Biotin | 0.52 g |

Cyanide hydratase activity can be induced by adding a source of cyanide ions and/or hydrogan cyanide to the culture as described in our co-pending UK Patent application No. 8604068. Such additions can be made separately or together with other nutrients throughout the cultivation of the cells. Preferably cyanide is added to the medium supplied to the process as alkali metal cyanides such as sodium or potassium cyanide. During startup of cultivation in a continuous process cyanide is best added initially in a low concentration which is gradually increased as the tolerance of the fungal cells in the culture towards it increases. Finally during steady state cultivation cyanide can be supplied at a concentration which is suitably at least 15 mM, in the total medium supplied to the culture, i.e. the sum of all the liquid feeds to the culture, preferably 2–10 (especially 4–6) m mole/g dry cell weight. We have found that higher concentrations of cyanide ions in the medium supplied to the culture during its steady state lead to increased activity of the cyanide hydratase enzyme in the cells and that the level of enzyme activity increases linearly with increases in the cyanide ion concentration. For example enzyme activity in units of $\mu$ mole formamide produced per minute per ml of culture at a low level (5 mM) of cyanide addition is 55 whereas the enzyme activity at a higher level (20 mM) is 220 units.

Preferred conditions for the cultivation part of the process are as follows:

dilution rate in the range 0.05 to 0.11 $hr^{-1}$; pH in the range 5.0 to 6.0, especially 5.5; and temperature in the range 28° to 34° C., especially 30° to 32° C. for highest enzyme activity, as described in our co-pending UK Patent application No. 8604068.

During the cultivation step in a continuous process, culture is continuously removed from the fermenter in which cultivation takes place and cells containing the enzyme cyanide hydratase are separated from the removed culture by any suitable means, filtration being preferred. The separated cells may then be dried and further treated, e.g. by extrusion, to produce cyanide hydratase-containing cellular material in any suitable form, e.g. in aggregates or as a powder. Whilst the enzyme could be separated from the cells and used in cell-free form, this is generally not necessary and the enzyme is usually not separated from the cells containing it. The fungal mycelia containing the cyanide hydratase can be immobilised as described in our European Patent No. 61249 but again this refinement is generally not carried out.

The cyanide hydratase material produced by the process of the invention is very suitable for the treatment of cyanide-containing aqueous effluents, e.g. by the process of our European Patent No. 61249. The enzyme produced has a high shelf-life stability (for example having a half life of up to 130 days) and a high activity. Enzyme-containing material having particularly high activity is produced when the cultivation step of the process is operated under conditions of oxygen limitation or of dual oxygen and carbon limitation. Activity is increased in cells grown at a temperature in the range 28° to 34° C. and especially in the range 30° to 32° C. An important advantage of the process is that the enzyme cyanide hydratase is produced in cells which are not pathogenic to the majority of common plants including arable crop plants such as wheat. The enzyme can thus be used in a wider range of applications than has been the case hitherto.

The invention is illustrated by the following Examples:

EXAMPLE 1

This was carried out to confirm that fungal strain *Fusarium lateritium* Nees CMI 300533 is non-pathogenic in the environment. To do this an investigation of the pathogenicity of this strain, two strains of *Fusarium graminearum* and a strain of *Fusarium culmorum* to winter wheat cultivars was made. Since the hosts of many of the wild type strains of the genus of which Fusarium strain CMI 300533 is a member, are small grain cereal crops it was decided to choose a highly susceptible wheat variety and to provide ideal conditions for disease induction. If disease could not be produced under these conditions this would indicate that the fungus was avirulent. The wheat varieties were chosen because of their sensitivity to *Fusarium culmorum*.

MATERIALS AND METHODS

For each isolate of Fusarium tested, 100 g dry wheat seed was inoculated with 5 ml of an aqueous suspension containing up to $2 \times 10^6$ conidia/ml. This was tumbled on a roller mill in a glass jar for 15 minutes and sown in either a paper towel or a soil test.

1. Paper Towel test 100 seeds were sown between 2 sheets of a special type of paper towel which were soaked in water, and placed in a polythene bag at 20° C. After 5–6 days stems of seedlings were examined for the presence of brown lesions which were dissected out and transferred onto agar. Plates were incubated at 25° C. for up to 7 days and the development of *F. lateritium* strain CMI 300533 and of the other strains was recorded.

2. Soil Test 100 seeds were sown between two seed trays ($22 \times 16 \times 5$ cm) in Levington Universal Compost and watered thoroughly; aluminium lids were placed over each pot. These were incubated at 10° C. for 8–10 days until the tips of the coleoptiles just emerged. The test was transferred to a glasshouse at 18° C. –25° C. for 4–6 days. Any brown lesions observed on the seedlings were dissected out and transferred onto agar. Plates were incubated at 25° C. for up to 7 days, and any development of *F. lateritium* strain CMI 300533 and of the other strains were recorded.

RESULTS

The response to inoculation of three cultivars of winter wheat by 4 isolates of Fusarium spp., including *F. lateritium* strain CMI 300533 is shown in the Table on page 10. *F. culmorum* infected all seedlings of the three varieties in both the paper towel and soil tests. *F. graminearum* isolates K57 and K1384 infected cultivar Rapier in the soil test. K1384 also infected cultivar Armada in the paper towel test. *F. lateritium* strain CMI 300533, was apparently not pathogenic to any of the three wheat cultivars.

TABLE

| | | | infection of winter wheat cultivars[a] by isolates of Fusarium Spp. | | | | | |
|---|---|---|---|---|---|---|---|---|
| | | Inoculum concentration | Paper Towel Test | | | Soil Test | | |
| Fusarium spp. | Isolate | (conidia/ml) | Armada | Brock | Rapier | Armada | Brock | Rapier |
| culmorum | K311D | $2 \times 10^6$ | + | + | + | + | + | + |
| | | $1 \times 10^6$ | + | + | + | + | + | + |
| lateritium | CMI 300533 | $1.2 \times 10^6$ | − | − | − | − | − | − |
| graminearum | K1384 | $0.12 \times 10^6$ | + | − | − | − | − | + |
| graminearum | K57 | $1.8 \times 10^6$ | − | − | − | − | − | + |

[a] + = infection, − = no infection } by Fusarium

CONCLUSIONS

1. This test was able to demonstrate the pathogenicity of isolates of *Fusarium culmorum* and *F. graminearum* to a highly susceptible variety of wheat.
2. Under the same conditions the *F. lateritium* strain CMI 300533 was not pathogenic.

EXAMPLE 2

*Fusarium lateritium* strain CMI 300533 was grown continuously in a 6000 l volume vessel using a defined medium containing glucose as carbon source, the glucose concentration being growth limiting. The pH was between 5.0 and 5.8, the dilution rate was 0.08 to 0.1 $hr^{-1}$ and the temperature was 30° to 32° C. Sodium cyanide was added to the nutrient feed at a concentration between 61.5 and 73.5 mM. The culture was subjected to oxygen stress by reduction of the aeration rate which resulted in the production of up to 0.81 g ethanol/l over a period of 140 hours. Biomass was produced at between 12.2 and 14.3 g/l with a cyanide hydratase activity of 81.0 to 122.4 μ moles formamide produced per minute per mg dry weight (assayed using 120 mM solutions of cyanide at pH 8.5 and 20° C.).

EXAMPLE 3

Fusarium strain CMI 300533 was grown continuously in a culture volume of 3 l using a defined medium containing glucose as carbon source and limiting nutrient. The pH was between 5.5 and 6.0; the dilution rate was 0.09–0.10 $h^{-1}$; the temperature was 30° C. During a 72 h period sodium cyanide solution was added to the nutrient at a concentration of 12.5 to 13.5 mM (in the total liquid feed) resulting in a cyanide hydratase activity of 19.5 to 25.5 μ moles/min/mg dry cell weight (assayed at pH 8.5 and at 20° C. in 100 mM sodium cyanide).

Also during this period a solution of propionitrile was added to the nutrient at 1.7 to 8.6 mM (in the total liquid feed).

The culture was sampled three times during this period and the supernatant was analysed for propionitrile, none being detected (limit of detection was 1 mM). As addition of propionitrile at that rate should have resulted in levels in the culture of 8.6 mM by the time of the last sample this indicates the presence of a nitrilase enzyme activity capable of degrading propionitrile.

I claim:

1. A process for the production of fungal cells containing the enzyme cyanide hydratase which comprises aerobically cultivating cells of a fungal strain selected from the group consisting of *Fusarium lateritium* Nees CMI 300533 and variants and mutants derived therefrom in an aqueous culture containing sources of carbon, appropriate inorganic nutrients and cyanide sufficient to induce production of the enzyme, and recovering fungal cells containing cyanide hydratase from the culture.

2. A process according to claim 1 wherein cultivation is carried out continuously under conditions selected from the group consisting of carbon limitation, oxygen limitation and dual carbon and oxygen limitation.

3. A process according to claim 1 which is continuous and wherein during cultivation the culture is continuously supplied with at least 15 mM cyanide in the form of either cyanide ions, hydrogen cyanide, or both.

4. A process according to claim 1 which is continuous and wherein during cultivation the culture is continuously supplied with at least 15 mM cyanide in the form of compounds which under the cultivation conditions used gererate either cyanide ions, hydrogen cyanide, or both.

5. A process according to claim 1 wherein the carbon source is glucose.

6. A process according to claim 2 wherein a source of either cyanide ion, hydrogen cyanide, or both is supplied to the culture at a concentration in the total medium in a range equivalent to 2–10 m mole/g dry cell weight.

7. A process according to claim 6 wherein the source of either cyanide ion, hydrogen cyanide, or both is supplied to the culture at a concentration in the total medium in a range equivalent to 4–6 m mole/g dry cell weight.

8. A process according to claim 1 wherein cultivation is carried out at a pH in the range 4.5 to 7.5.

9. A process according to claim 1 wherein cultivation is carried out at a temperature in the range 28° to 34° C.

10. A method for the treatment of a cyanide-containing material to degrade the cyanide therein in which the cyanide-containing material is treated with cyanide hydratase present in or derived from fungal cells produced by a process according to claim 1.

11. A process for the production of fungal cells containing a nitrilase enzyme which comprises aerobically cultivating cells of a fungal strain selected from the group consisting of *Fusarium lateritium* Nees CMI 300533 and variants and mutants derived therefrom in an aqueous culture containing sources of carbon, appropriate inorganic nutrients and cyanide sufficient to induce production of the enzyme, and recovering fungal cells containing a nitrilase enzyme and cyanide hydratase from the culture.

* * * * *